US00PP21424P2

(12) United States Plant Patent
Cornelis

(10) Patent No.: US PP21,424 P2
(45) Date of Patent: Oct. 26, 2010

(54) *SPATHIPHYLLUM* PLANT NAMED 'DELTA'
(50) Latin Name: ***Spathiphyllum* hybrid**
Varietal Denomination: Delta

(76) Inventor: Daniel Cornelis, Oude Gaverweg 2, Melsem-Merelbeke (BE) B-9820

( * ) Notice: Subject to any disclaimer, the term of this patent is extended or adjusted under 35 U.S.C. 154(b) by 0 days.

(21) Appl. No.: 12/459,822

(22) Filed: Jul. 7, 2009

(51) Int. Cl.
*A01H 5/00* (2006.01)

(52) U.S. Cl. ..... Plt./364

(58) Field of Classification Search ..... Plt./364
See application file for complete search history.

*Primary Examiner*—Annette H Para
*Assistant Examiner*—Louanne C Krawczewicz Myers

(57) ABSTRACT

A new and distinct *Spathiphyllum* cultivar named 'DELTA' is disclosed, characterized by moderate spathe production, very large, pure white spathe color, without cream coloration. The new variety is commercially suitable for indoor plant production.

1 Drawing Sheet

Figure 1:
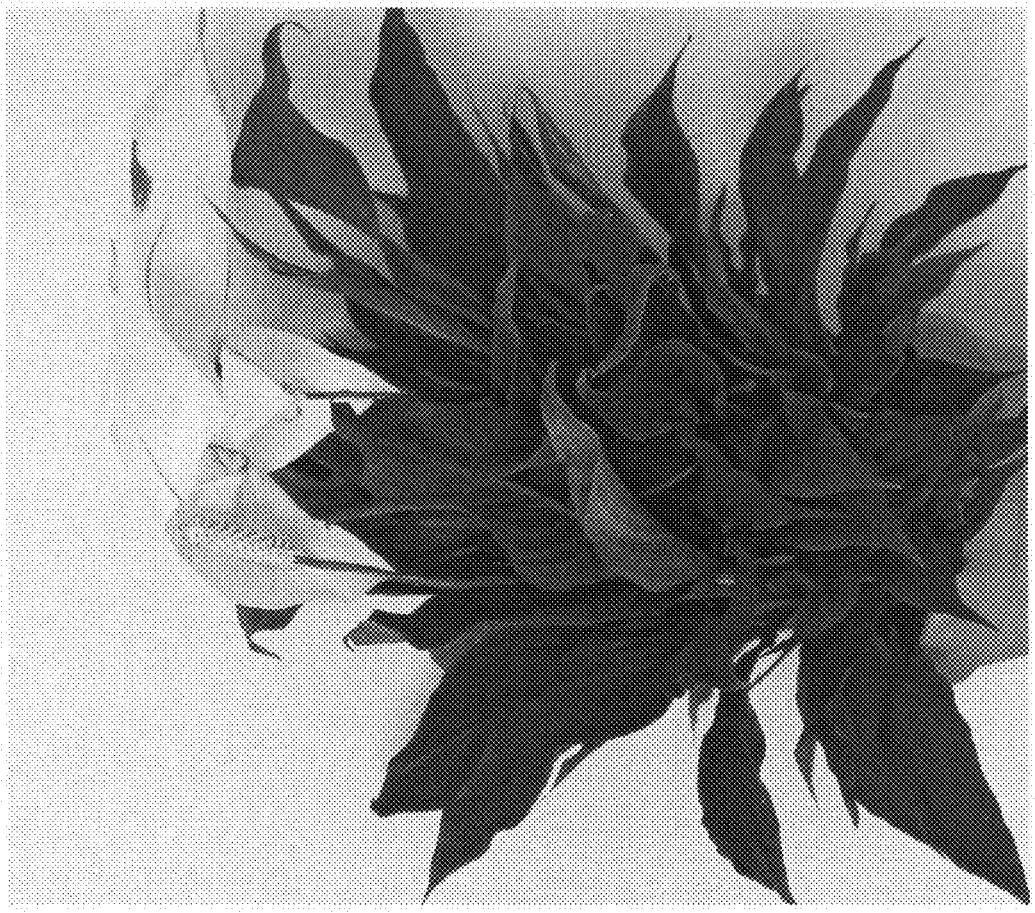

Latin name of the genus and species: *Spathiphyllum* hybrid.

Variety denomination: 'DELTA'.

BACKGROUND OF THE INVENTION

The new cultivar is a product of a planned breeding program. The new variety originated from a cross pollination, made by the inventor in February 2005 at a commercial greenhouse in Melsem-Merelbeke, Belgium, of the seed parent, a proprietary *Spathiphyllum* hybrid and the pollen parent a proprietary *Spathiphyllum* hybrid. The identifiers and specific information regarding the parents is unavailable because the inventor has lost the records regarding the specific parents used in the February 2005 crossing.

The new variety was discovered by the inventor, Daniel Cornelis, a citizen of Belgium, in December 2006 in a group of seedlings resulting from the crossing. The new cultivar was found in a commercial greenhouse belonging to the inventor in Melsem-Merelbeke, Belgium.

Asexual reproduction of the new cultivar 'DELTA' was first performed at a commercial laboratory in the Netherlands by tissue culture in June 2007. 'DELTA' has been reproduced by micro-propagation and has shown that the unique features of this cultivar are stable and reproduced true to type.

SUMMARY OF THE INVENTION

The cultivar 'DELTA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DELTA.' These characteristics in combination distinguish 'DELTA' as a new and distinct *Spathiphyllum* cultivar:

1. Moderate spathe production.
2. Very large spathes.
3. Bright white spathe color, without cream coloration.
4. Broad leaves, making a full, bushy plant.

COMMERCIAL COMPARISON

Plants of the new cultivar 'Delta' are similar to plants of the patented variety, *Spathiphyllum* hybrid 'Alfa CD' U.S. Plant Pat. No. 10,823 in most horticultural characteristics, however, plants of the new cultivar produce larger spathes, a fuller bushier plant and wider leaves than 'Alfa CD'.

BRIEF DESCRIPTION OF THE PHOTOGRAPH

The accompanying photograph in FIG. 1 illustrates in full color a typical plant of 'DELTA' grown in a greenhouse in Apopka, Fla. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DELTA' plants grown in a climate controlled greenhouse in Apopka, Fla., USA. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Spathiphyllum* hybrid cultivar 'DELTA'.

PROPAGATION

Time to initiate roots: Approximately 8 days from a tissue culture plantlet at approximately 20 to 22° C.

Time to produce rooted plantlet: Approximately 7 weeks at approximately 20 to 22° C.

Root description: Fine, fibrous.

PLANT

Growth habit: Leaves growing directly from base of plant, forming a round plant shape.

Plant Shape: Upright, leaves slightly arching out.

Height: Approximately 45 cm to top of highest leaf, approximately 60 cm to top of highest spathe. Measurements from top of soil level in pot.

Plant spread: Approximately 55 cm in a 6 inch pot.
Normal pot size: 6 inch, 8 inch and larger.
Growth rate: Moderate.
Branching characteristics: No branching. Leaves emerge direct from base of plant.
Number of clumps of leaves: 12.
Number of leaves per clump: Average 15.
Number of leaves per plant: Approximately 180.
Age of plant described: Approximately 9 months.

FOLIAGE

Leaf:
- *Arrangement.*—Single leaves emerging basally.
- *Average Length(excluding petiole)*: Approximately 30 cm.
- *Average Width.*—Approximately 13.5 cm.
- *Shape of blade.*—Oblong.
- *Aspect.*—Slightly recurved and slightly undulating.
- *Apex.*—Apiculate
- *Base.*—Attenuate
- *Margin.*—Entire.
- *Texture of top surface.*—Smooth, moderately glossy.
- *Texture of bottom surface.*—Smooth, moderately glossy.
- *Color.*—Young foliage upper side: Near R.H.S. Green 137A. Young foliage under side: Near R.H.S. Green 138A. Mature foliage upper side: Near R.H.S. Green 139A. Mature foliage under side: Near R.H.S. Green 137A.

Venation:
- *Type.*—Pinnate.
- *Venation coloration upper side.*—Near RHS Yellow-Green 144A.
- *Venation coloration under side.*—Near RHS Yellow-Green 144A.

Petiole(excluding geniculum):
- *Length.*—Approximately 11.5 cm.
- *Width.*—At geniculum: Approximately 0.6 cm. Above clump: Approximately 1.2 cm.
- *Color.*—Near RHS Green 137B.
- *Strength.*—Very strong.

Geniculum:
- *Length.*—Approximately 9.5 cm.
- *Width.*—Approximately 1.1 cm.
- *Color.*—Near RHS Green 137B.
- *Other characteristics.*—Tightly held to and entirely rolled around to petiole.

INFLORESCENCE

- *Arrangement.*—Spathes with spadices held above the foliage on erect peduncles arising from the petiole sheath.
- *Flowering habit.*—Continuous.
- *Quantity of spathes per plant.*—On average 5 to 6 fully open spathes with approximately 8 beginning to emerge.
- *Natural flowering season.*—Autumn to Winter.
- Time to flowering.—Approximately 6 months.
- *Fragrance.*—Sweet, moderately strong.
- *Self-cleaning or persistent.*—Persistent.
- *Flower Longevity.*—Flowers stay in good condition approximately 6 weeks on the plant.

Spathe:
- *Aspect.*—Concave.
- *Length.*—Approximately 25 cm.
- *Width.*—Approximately 12 cm.
- *Shape.*—Obovate.
- *Margin.*—Entire.
- *Apex.*—Apiculate.
- *Base.*—Attenuate.
- *Color.*—Front when opening: Near RHS White 155C. Back when opening: Near RHS White 155C. Front when mature: Near RHS White 155C. Back when mature: Near RHS White 155C. Fading to: Near RHS White 155C. Occasional blotches with age near Greyed-Orange 166A.

Spadix:
- *Shape.*—Columnar, arising from the top of the peduncle.
- *Tip.*—Obtuse.
- *Base.*—Obtuse.
- *Length.*—Approximately 9.5 cm.
- *Width.*—Approximately 2.1 cm.
- *Color.*—When opening: Near RHS White 155A. Mature: Near RHS White 155C.
- *Quantity of flowers per spadix.*—Approximately 215.
- *Spadix flower arrangement.*—Bisexual, rounded.
- *Spadix flower diameter.*—Approximately 0.3 cm.
- *Spadix flower depth.*—Approximately 0.5 cm.

Peduncle:
- *Length.*—Approximately 30 cm.
- *Width.*—Approximately 0.8 cm.
- *Color.*—Near RHS Green 137A.
- *Strength.*—Very strong.

REPRODUCTIVE ORGANS

All parts are highly compact and indistinguishable. Moderate pollen appears on spadix with age. Pollen color Near RHS White 155C.

OTHER CHARACTERISTICS

Disease resistance: Neither resistance nor susceptibility to diseases or pests has been observed in this variety to date.
Drought tolerance and cold tolerance: The new cultivar is a typical *Spathiphyllum*, cold tolerant to approximately 5 to 7° C. and does not tolerate drought.
Fruit/seed production: Not observed to date.

What is claimed is:

1. A new and distinct cultivar of *Spathiphyllum* plant named 'DELTA' as herein illustrated and described.

* * * * *